United States Patent [19]

Freyne et al.

[11] Patent Number: 5,180,832

[45] Date of Patent: Jan. 19, 1993

[54] (3-PYRIDINYL)METHANONE OXIME DERIVATIVES

[75] Inventors: Eddy J. E. Freyne, Rumst; Alfons H. M. Raeymaekers, Beerse; Victor Sipido, Merksem, all of Belgium; Marc G. Venet, Paris, France

[73] Assignee: Janssen Pharmaceutica N.V., Beerse, Belgium

[21] Appl. No.: 583,758

[22] Filed: Sep. 17, 1990

Related U.S. Application Data

[60] Division of Ser. No. 356,592, May 23, 1989, Pat. No. 4,963,573, which is a continuation of Ser. No. 156,513, Feb. 16, 1988, abandoned, which is a continuation of Ser. No. 888,670, Jul. 23, 1986, Pat. No. 4,746,671, which is a continuation-in-part of Ser. No. 794,999, Nov. 4, 1985, abandoned.

[51] Int. Cl.⁵ .................. C07D 213/53; C07D 213/46
[52] U.S. Cl. .................. 546/333; 546/264; 546/283; 546/284; 546/335
[58] Field of Search .................. 546/333

[56] References Cited

PUBLICATIONS

Villani et al., Journal of Organic Chemistry, vol. 40(12), Jun. 13, 1975.
Chem. Abstracts, vol. 86(11), Abst. No. 86: 72449b, Mar. 14, 1977.
Chem. Abstracts, vol. 66(19), Abst. No. 85680g, May 8, 1967.

*Primary Examiner*—Alan L. Rotman
*Attorney, Agent, or Firm*—Charles J. Metz

[57] ABSTRACT

Novel [[[(3-pyridinyl)methylen]amino]oxy]alkanoic acids and esters, compositions containing the same, and methods of treating clinical conditions related with the production of thromboxane $A_2$, prostacyclin and/or prostaglandin s $D_2$, $E_3$ and $F_{2\alpha}$.

9 Claims, No Drawings

(3-PYRIDINYL)METHANONE OXIME DERIVATIVES

CROSS-REFERENCE TO RELATED APPLICATIONS

This application is a division of application Ser. No. 356,592, filed on May 23, 1989, now U.S. Pat. No. 4,963,573, which was a continuation of application Ser. No. 156,513, filed on Feb. 16, 1988, now abandoned, which was a continuation of application Ser. No. 888,670, filed on Jul. 23, 1986, now U.S. Pat. No. 4,746,671, which was a continuation-in-part of application Ser. No. 794,999, filed on Nov. 4, 1985, now abandoned.

BACKGROUND OF THE INVENTION

A number of [[(3-pyridinyl)methylen]amino]oxy derivatives have been described in J. Chem. Soc., Perkin Trans. I. (3), 984-7 (1981) and in J. Med. Chem. 7 (6), 824-6 (1964) as intermediates or as compounds having plant growth inhibitory and vitamin K activity.

In Swiss Patent No. 616,406 there are described a number of [[(3-pyridinyl)methylen]amino]oxy derivatives which are useful as lipid lowering and plant protective agents.

In U.S. Pat. No. 4,518,602 there are described a number of vinylcarboxylic acid derivatives with thromboxane $A_2$ synthetase inhibitory properties.

In the Published European Patent Application No. 0,175,304, there are described [[(methylen)amino]oxy]-propanoic acids.

The compounds of the present invention differ from the cited prior-art compounds by their capability of specifically inhibiting the enzymatic synthesis of thromboxane $A_2$ and by the nature of the substituents attached to the [(methylen)amino]oxy group.

DESCRIPTION OF THE PREFERRED EMBODIMENTS

This invention is concerned with novel [[[(3-pyridinyl)methylen]amino]oxy]alkanoic acids and esters which may structurally be represented by the formula

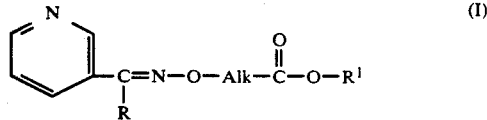

the N-oxides, the pharmaceutically acceptable acid-addition, metal or amine substitution salts and the possible stereochemically isomeric forms thereof, wherein:
R is hydrogen, $C_{1-10}$alkyl, trifluoromethyl, Ar or Ar(-$C_{1-10}$-alkyl); wherein Ar is phenyl, naphthalenyl, pyridinyl, pyrimidinyl, furanyl or thienyl, said phenyl and naphthalenyl are each optionally substituted with up to 3 substituents being each independently $C_{1-6}$alkyl, $C_{1-6}$alkyloxy, mono- and di($C_{1-6}$alkyloxy)methyl, amino, $C_{1-6}$alkylcarbonylamino, carboxyl, formyl, halo, hydroxy, nitro or trifluoromethyl;
$R^1$ is hydrogen or $C_{1-6}$ alkyl; and
Alk is a $C_{2-10}$ alkanediyl radical;
provided that the [[(3-pyridinyl)methylen]amino]oxy radical and the —$COOR^1$ radical are not bound to the same carbon atom.

In the foregoing definitions the term halo is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; "$C_{1-10}$ alkyl" is meant to include straight and branched saturated hydrocarbon radicals, having from 1 to 10 carbon atoms; and "$C_{2-10}$ alkanediyl" is meant to include bivalent straight or branch chained alkanediyl radicals having from 2 to 10 carbon atoms.

The said N-oxides of the compounds of formula (I) are meant to comprise those compounds of formula (I) wherein one or more nitrogen atoms, preferably pyridine nitrogen atoms, are oxidated to the so called N-oxide form.

Preferred compounds within the present invention are those wherein the [[(3-pyridinyl)methylen]amino]oxy radical and the —$COOR^1$ radical are separated by at least 3 and at most 6 carbon atoms.

Particularly preferred compounds are those preferred compounds wherein R is Ar or Ar($C_{1-4}$alkyl).

More particularly preferred compounds are those particularly preferred compounds wherein $R^1$ is hydrogen and R is phenyl or naphthalenyl wherein said phenyl and naphthalenyl are each optionally substituted with up to 2 substituents being each independently $C_{1-6}$alkyl, $C_{1-6}$alkyloxy, di($C_{1-6}$alkyloxy)methyl, formyl, halo or trifluoromethyl.

Especially preferred compounds within the invention are those more particularly preferred compounds wherein the pyridine ring and the —O—Alk—$COOR^1$ substituents on the oxime moiety are in a trans configuration.

The most preferred compounds are selected from the group consisting of (E)-5-[[[(3-pyridinyl) [3-(trifluoromethyl)phenyl]methylen]amino]oxy]pentanoic acid and (E)-5-[[[(3-methylphenyl)(3-pyridinyl)methylen]amino]oxy]pentanoic acid the pharmaceutically acceptable salts and the N-oxide forms thereof.

The compounds of formula (I) may generally be prepared by the reaction of an oxime of formula (II) or its N-oxide with an intermediate of formula (III) following art-known o-alkylation procedures.

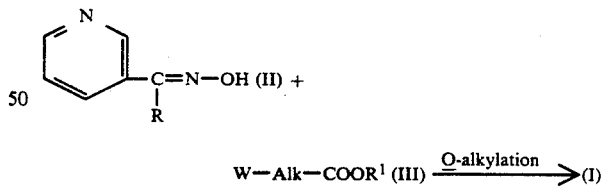

In (III) W represents an appropriate reactive leaving group such as, for example, halo, e.g., chloro, bromo or iodo, or a sulfonyloxy group, e.g. methylsulfonyloxy or 4-methylphenylsulfonyloxy.

The o-alkylation reactions are conveniently conducted in a suitable reaction-inert solvent or a mixture of such solvents. A suitable reaction-inert solvent may, for example, be an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; a polar aprotic solvent, e.g., N,N-dimethylformamide (DMF), N,N-dimethylacetamide (DMA), hexamethylphosphoric triamide (HMPT), dimethyl sulfoxide (DMSO), nitrobenzene, 1-methyl-2-pyrrolidinone, and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

It may be advantageous to convert previously the oxime of formula (II) into a metal salt form thereof, preferably the alkali metal salt form, by reacting the starting oxime with, for example, an alkali metal hydride or an earth alkaline metal hydride, e.g., sodium hydride, calcium hydride and the like or an alkali metal hydroxide, e.g., sodium hydroxide, potassium hydroxide and the like, and to use thereafter said metal salt form in the reaction with (III).

The compounds of formula (I) can also be prepared by reacting an aldehyde or ketone of formula (IV) or its N-oxide with an (amino)oxy acid or ester of formula (V), or preferably an acid addition salt form thereof; or where $R^1$ is hydrogen, the alkalimetal salt form of (V) may most conveniently be used.

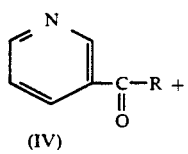

(IV)

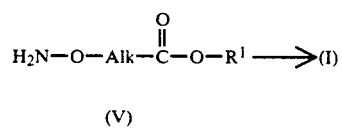

(V)

The reaction of (IV) with (V) may be conducted in a suitable reaction-inert solvent such as, for example, water; a lower alkanol, e.g. methanol, ethanol, 1-butanol and the like; an ether, e.g., 1,4-dioxane, 1,1'-oxybisethane, tetrahydrofuran and the like or an aromatic hydrocarbon, e.g., benzene, methylbenzene, dimethylbenzene and the like; and mixtures of such solvents. The addition of an appropriate base such as, for example, an alkali metal hydroxide, carbonate or hydrogen carbonate or an organic base such as, for example, a tertiary amine, e.g., N,N-diethylethanamine, N-(1-methylethyl)-2-propanamine and the like or pyridine may be preferred.

compounds of formula (I) can also be prepared by transoximation of an aldehyde or ketone of formula (IV) or its N-oxide and an oxime of formula (VI). Said transoximation reaction may conveniently be carried out by stirring and, if desired, heating the reactans together in an acidic solvent. The by-product aldehyde or ketone of formula (VII) is preferably removed from the reaction mixture following art-known procedures such as, for example, by fractional destillation and the like.

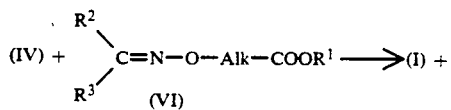

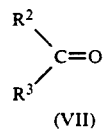

(VII)

said $R^2$ and $R^3$ in formula (VI) and (VII) are each independently hydrogen or $C_{1-6}$alkyl.

The compounds of formula (I) may also be prepared by reacting an alkene of formula (VIII) with an oxime of formula (II) or its N-oxide in a suitable solvent in the presence of a catalytic amount of an appropriate base.

The compounds of formula (I) can also be converted into each other following art-known procedures of functional group transformation. Some examples will be cited hereinafter.

The compounds of formula (I) containing an ester group may be converted into the corresponding carboxylic acids following art-known saponification procedures, e.g., by treating the starting compounds with an aqueous alkaline or an aqueous acidic solution.

Vice versa, the carboxylic acid group may be converted into the corresponding ester group following art-known esterification procedures. For example, the carboxylic acid may be converted into a reactive derivative which subsequently, is reacted with the corresponding alkanol $HOR^1$; or by reacting the carboxylic acid and the alkanol $HOR^1$ with a suitable reagent capable of forming esters, e.g., dicyclohexylcarbodiimide, 2-chloro-1-methylpyridinium iodide and the like.

The compounds of formula (I) having a nitro substituent may be converted into the corresponding amines by art-known nitro-to-amine reduction procedures, such as, for example, stirring in the presence of sodium dithionite.

The amino substituent may, if desired, be further converted into compounds of formula (I) having a $C_{1-6}$alkylcarbonylamino substituent by reacting the amine with a suitable acylating agent, e.g. an acyl halide or an acid anhydride.

Compounds of formula (I) having a di($C_{1-6}$alkoxy)-methyl substituent may be deacetalized to yield the corresponding formyl group. Said deacetalization may be conducted following procedures widely known in the art such as, for example, by reacting the starting materials in an acidic aqueous medium.

Said formyl group may be further oxidated into the corresponding carboxyl group with an appropriate oxidans e.g. potassium permanganate, silver(I) oxide and the like.

The compounds of formula (I) can be converted to the corresponding N-oxide forms following art known procedures for converting a pyridinyl nitrogen to its N-oxide form. Such N-oxidation reaction may generally be carried out by reacting the starting compound with an appropriate organic or inorganic peroxide. Appropriate inorganic peroxides can, for example, be hydrogen peroxide, an alkali metal or earth alkaline metal peroxide, e.g. sodium peroxide, potassium peroxide, barium peroxide and the like; appropriate organic peroxides may comprise peroxy acids such as, for example, benzenecarboperoxoic acid or halo substituted benzenecarboperoxoic acid, e.g. 3-chlorobenzenecarboperoxoic acid and the like, peroxoalkanoic acids, e.g. peroxoacetic acid and the like, alkylhydroperoxides, e.g. t.butyl hydroperoxide and the like. Suitable solvents are, for example, water, lower alkanols, e.g. methanol, ethanol, propanol, butanol and the like, hydrocarbons, e.g. benzene, methylbenzene, dimethylbenzene and the like, ketones, e.g. 2-propanone, 2-butanone and the like, halogenated hydrocarbons, e.g. dichloromethane, trichloromethane and the like, and mixtures of such solvents. In order to enhance the reaction rate, it may be appropriate to heat the reaction mixture.

In all of the foregoing and the following preparations, the reaction products may be isolated from the reaction mixture and, if necessary, further purified according to methodologies generally known in the art.

From formula (I) it is evident that the compounds of this invention may be present as E- or Z-forms, this E and Z notation being in correspondence with the rules described in "International Union of Pure and Applied Chemistry: Tentative Rules for the Nomenclature of Organic Chemistry. Section E. Fundamental Stereochemistry" in J. Org. Chem., 35, 2849–2867 (1970).

Depending on the nature of the substituents on the oxime moiety it may be advantageous to subject a given mixture of E- and Z-isomers to an isomerization reaction before separation of the pure geometric isomers. Said isomerization reaction is an equilibrium reaction which is generally conducted in the presence of a mineral acid.

Pure stereochemically isomeric forms of the compounds of formula (I) and intermediates of formula (II) may be obtained by the application of art-known separation methods such as selective crystallization and chromatographic techniques, e.g., counter current distribution, column chromatography, high performance liquid chromatography and the like.

Stereochemically isomeric forms of the compounds of formula (I) are naturally intended to be embraced within the scope of the invention.

The compounds of formula (I) may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 3-phenyl-2-propenoic, α-hydroxybenzeneacetic, 2-hydroxybenzoic, 4-amino-2-hydroxybenzoic and the like acids. Conversely the salt form can be converted by treatment with alkali into the free base form.

The compounds of formula (I) containing one or more acidic protons, may also be converted to their therapeutically active non-toxic metal or amine substitution salt forms by treatment with appropriate organic or inorganic bases. Appropriate inorganic bases may, for example, be ammonia or bases derived from alkali or earth alkaline metals, e.g. alkali metal or earth alkaline metal oxides or hydroxides such as lithium hydroxide, sodium hydroxide, potassium hydroxide, magnesium hydroxide, calcium hydroxide, calciumoxide and the like; alkalimetal or earth alkaline metal hydrides, e.g.

sodium hydride, potassium hydride and the like; alkalimetal hydrogen carbonates or carbonates, e.g. sodium carbonate, potassium carbonate, sodium hydrogen carbonate, calcium carbonate and the like. Appropriate organic bases may, for example be primary, secondary and tertiary aliphatic and aromatic amines such as, for example, methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, N-methylmorpholine, trimethylamine, tripropylamine, quinuclidine, pyridine, quinoline, isoquinoline, diethanolamine and 1,4-diazabicyclo[2,2,2]octane; or quaternary ammonium bases e.g. tetramethylammonium hydroxide, trimethylbenzylammonium hydroxide, triethylbenzylammonium hydroxide, tetraethylammonium hydroxide, and trimethylethylammonium hydroxide. Conversely the salt form can be converted by treatment with an acid into the free acidic form.

Some intermediates and starting materials in the foregoing preparations are known compounds which may be prepared according to art-known methodologies of preparing acid or similar compounds. A number of such preparation methods will be described hereinafter in more detail.

The intermediates of formula (II) can easily be derived from the corresponding carbonyl compounds of formula (IV) or its N-oxide by reacting the latter with hydroxylamine (IX) or an acid addition salt form thereof according to the procedures described hereinabove for the preparation of (I) starting from (IV) and (V).

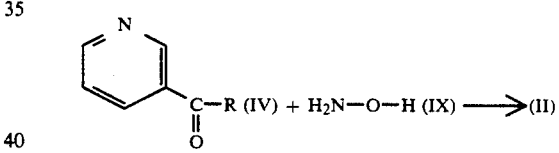

The intermediates of formula (V) can conveniently be prepared following art-known procedures as described in, for example, Tetrahedron 23, 4441–7 (1967).

The compounds of formula (I), their N-oxide forms, their acid addition, metal or amine substitution salts or stereochemically isomeric forms possess useful pharmacological properties, said useful pharmacological properties can be demonstrated for example, in the "Platelet malondialdehyde (MDA) production" test, described hereinafter, illustrating the thromboxane synthetase inhibitory properties of the compounds of the present invention. In addition to the above, the selective inhibitory action on the bio-synthesis of thromboxane $A_2$ and the increasing effect on the production of prostacyclin and prostaglandin $D_2$, $E_2$ and $F_{2\alpha}$ may, for example, be demonstrated in blood platelet aggregation experiments using various inducers, such as, for example, collagen, arachidonic acid and the like; or in experiments measuring the intermediates in the arachidonic acid metabolism using labelled arachidonic acid or radio-immunoassays.

In view of their useful pharmacological properties, the subject compounds may be formulated into various pharmaceutical forms for administration purposes. To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

The compounds of formula (I), their N-oxides, their pharmaceutically acceptable acid-addition, metal or amine substitution salts and their possible stereochemically isomeric forms, show a selective inhibitory action on the bio-synthesis of thromboxane $A_2$ and also an increasing effect on the production of prostacyclin and prostaglandin $D_2$, $E_2$ and $F_{2\alpha}$, acting as well on the blood platelets as on the vessel wall.

In view of their capability to inhibit selectively the bio-synthesis of thromboxane $A_2$, and their increasing effect on the production of prostacyclin and prostaglandin $D_2$, $E_2$ and $F_{2\alpha}$ compounds of the present invention can be used as inhibitors of vasoconstriction and of blood platelet aggregation, which effects are known to be affected by thromboxane $A_2$, prostacyclin, and/or prostaglandin $D_2$, $E_2$ and $F_{2\alpha}$ (Science, 193, 1135–1137 (1976), Pharmacolog. Rev., 30, 293–331 (1979)).

In view of the utility of the compounds of formula (I), their N-oxides, their pharmaceutically acceptable acid-addition, metal or amine substitution salts and their possible stereochemically isomeric forms, there is provided a method of treating several clinical conditions in mammals, which conditions are related to the production of thromboxane $A_2$, prostacyclin, and/or prostaglandin $D_2$, $E_2$ and $F_{2\alpha}$. Said clinical conditions may, for example, be thrombosis in various vascular beds or ischaemic diseases e.g. ischaemic heart disease, angina pectoris, stroke, transient ischaemic attack, migraine, ischaemic disease in the kidney, lung and other organs, peptic ulcer, vascular complications of diabetes, and cancer and its dissimination through the blood stream. This method comprises the systemic administration to mammals of an effective amount of a compound of formula (I), a N-oxide, a pharmaceutically acceptable acid-addition, metal or amine substitution salt or a possible stereochemically isomeric form thereof.

Those of skill in treating the said clinical conditions could easily determine the effective amount from the test results presented hereinafter. In general it is contemplated that an effective amount would be from 0.005 mg/kg to 20 mg/kg body weight, and more preferably from 0.01 mg/kg to 10 mg/kg body weight.

The following examples are intended to illustrate and not to limit the scope of the present invention. Unless otherwise stated all parts therein are by weight.

EXPERIMENTAL PART

A. Preparation Of Intermediates

EXAMPLE 1

To a stirred and cooled ($-78°$ C.) mixture of 50 parts of 1-bromo-2-(dimethoxymethyl)benzene and 245 parts of 1,1'-oxybisethane were added dropwise 59 parts of a 1-butyllithium solution 2.5M in hexane. Upon complete addition, stirring was continued for 10 minutes at room temperature. A solution of 23.1 parts of 3-pyridinecarboxaldehyde in 42 parts of 1,1'-oxybisethane was added dropwise to the reaction mixture. Upon completion, the mixture was allowed to reach room temperature. The mixture was taken up in ice water and the product was extracted with 1,1'-oxybisethane. The extract was dried, filtered and evaporated, yielding 56 parts (99.9%) of α-[2-(dimethoxymethyl)phenyl]-3-pyridinemethanol as a residue (intermediate 1).

In a similar manner there was also prepared: α-[3-(dimethoxymethyl)phenyl]-3-pyridinemethanol as a residue (intermediate 2).

EXAMPLE 2

To a stirred and cooled ($-70° \sim -80°$ C.) solution of 71.4 parts of a 1-butyllithium solution 1.6M in hexane in 105 parts of 1,1'-oxybisethane was added dropwise a solution of 40.6 parts of 3-bromopyridine in 70 parts of 1,1'-oxybisethane. Upon complete addition, stirring was continued for 15 minutes and a solution of 30 parts of 2-(trifluoromethyl)benzonitrile in 35 parts of 1,1'-oxybisethane was added dropwise at this low temperature. Upon completion, the mixture was stirred for 3 hours at this low temperature. The mixture was heated to room temperature and poured into 84 parts of a hydrochloric acid solution 10N and some crushed ice. The aqueous layer was separated and heated to the boiling point.

After cooling, the mixture was made alkaline with an ammonium hydroxide solution and the product was extracted with dichloromethane. The extract was dried, filtered and concentrated. The residue was purified by filtration over silica gel using trichloromethane as eluent. The pure fractions were collected and the eluent was concentrated, yielding 27.8 parts (63%) of (3-pyridinyl) [2-(trifluoromethyl)phenyl]methanone as an oily residue (intermediate 3).

In a similar manner there was also prepared: [3,5-bis(-trifluoromethyl)phenyl] (3-pyridinyl)methanone as a residue (intermediate 4).

EXAMPLE 3

To a stirred mixture of 12 parts of magnesium and 70 parts of 1,1'-oxybisethane were added dropwise 88 parts of 1-bromooctane while cooling and under nitrogen atmosphere. Upon complete addition, the mixture was heated for 1 hour at reflux temperature. 1,1'-Oxybisethane was removed and a mixture of 40 parts of 3-pyridinecarbonitrile and 180 parts of benzene was added. The whole was heated for 2 hours at reflux and after cooling, the mixture was poured into 300 parts of ice water. The separated aqueous phase was treated with ammonium hydroxide and the product was extracted three times with 150 parts of trichloromethane. The combined extracts were dried, filtered and evaporated, yielding 70.7 parts (83.9%) of 1-(3-pyridinyl)-1-nonanone as a residue (intermediate 5).

EXAMPLE 4

A mixture of 19 parts of α-[3-(dimethoxymethyl)-phenyl]-3-pyridinemethanol, 36 parts of activated mangenese (IV) oxide and 280 parts of dichloromethane was stirred over weekend at room temperature. The reaction mixture was filtered over silica gel and the filtrate was filtered again over diatomaceous earth and silica gel. The filtrate was evaporated and the residue was distilled in vacuo. The desired fraction was collected, yielding 15.7 parts (82% of [3-(dimethoxymethyl)phenyl] (3-pyridinyl)methanone (intermediate 6).

In a similar manner there was also prepared: [2-(dimethoxymethyl)phenyl] (3-pyridinyl)methanone: bp. 142°~147° C. (intermediate 7).

EXAMPLE 5

To a stirred and cooled (0° C.) solution of 70 parts of 2-phenyl-1-(3-pyridinyl)ethanone in 225 parts of N,N-dimethylformamide were added dropwise 46.9 parts of 2-methyl-2-propanol, potassium salt under nitrogen atmosphere. Upon complete addition, stirring was continued for 30 minutes at 0° C. The reaction mixture was allowed to reach room temperature and 70 parts of iodomethane were added. The reaction mixture was allowed to stand at room temperature for 8 hours. The mixture was poured into water and the product was extracted with 1,1'-oxybisethane. The extract was washed with water, dried, filtered and evaporated to dry, yielding 30 parts (40%) of 2-phenyl-1-(3-pyridinyl)-1-propanone as a residue (intermediate 8).

EXAMPLE 6

A mixture of 27.6 parts of [3-(trifluoromethyl)-phenyl](3-pyridinyl)ethanone, 8.3 parts of hydroxylamine hydrochloride, 6.4 parts of sodium carbonate and 160 parts of ethanol was stirred for 24 hours at reflux temperature. After cooling, the precipitated product was filtered off (set aside) and washed with water. The ethanol layer was concentrated and the remaining residue was also washed with water, combined with the first fraction which was set aside (see above) and crystallized from 120 parts of 4-methyl-2-pentanone. The product was filtered off and dried, yielding 20 parts (68%) of (E+Z)-(3-pyridinyl) [3-(trifluoromethyl)-phenyl]methanone, oxime; mp. 185.4° C. (intermediate 9).

In a similar manner there were also prepared:

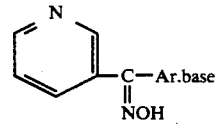

| No. | Ar | isomeric form | mp.(°C.) |
|---|---|---|---|
| 10 | 4-Cl—C$_6$H$_4$— | E + Z | 151.0 |
| 11 | 4-CH$_3$—C$_6$H$_4$— | E + Z | 164.4 |
| 12 | 4-F—C$_6$H$_4$— | E + Z | |
| 13 | 1-naphthalenyl | E + Z | 175.3 |
| 14 | 2-naphthalenyl | E + Z | |
| 15 | 4-NO$_2$—C$_6$H$_4$— | E + Z | 218 |
| 16 | 3,4-(OCH$_3$)$_2$—C$_6$H$_3$— | E + Z | 151.1 |
| 17 | 3-thienyl | E + Z | |

EXAMPLE 7

A mixture of 70 parts of 1-(3-pyridinyl)-1-nonanone, 44.8 parts of hydroxylamine hydrochloride, 88.2 parts of potassium carbonate and 320 parts of ethanol was stirred for 2 hours at reflux temperature. After evaporation to dry, the residue was poured into 1000 parts of water and the product was extracted three times with 105 parts of 1,1'-oxybisethane. The combined extracts were dried, filtered and evaporated, yielding 68.5 parts (91.6%) of 1-(3-pyridinyl)-1-nonanone,oxime as a residue (intermediate 18).

In a similar manner there were also prepared: 1-(3-pyridinyl)-1-heptanone,oxime as a residue (intermediate 19); and (E+Z)-2-phenyl-1-(3-pyridinyl)-1-propanone,oxime (intermediate 20).

EXAMPLE 8

To a stirred mixture of 4.3 parts of (4-methoxyphenyl) (3-pyridinyl)ethanone, 1.53 parts of hydroxylamine hydrochloride and 80 parts of ethanol were added dropwise 2.1 parts of N,N-diethylethanamine at room temperature. Upon complete addition, stirring was continued overnight at reflux temperature. The reaction mixture was evaporated. The residue was taken up in water while stirring. The product was filtered off, washed with water and crystallized twice: first from acetonitrile and then from ethyl acetate. The product was filtered off, washed with ethyl acetate and 2,2'-oxybispropane and dried in vacuo at 60° C., yielding 1.68 parts (36.8%) of (E+Z)-(4-methoxyphenyl) (3-pyridinyl)methanone,oxime; mp. 176.0° C. (intermediate 21).

EXAMPLE 9

To a stirred mixture of 54.2 parts of (3-methylphenyl) (3-pyridinyl)methanone, 25.2 parts of sodium hydrogen carbonate and 480 parts of ethanol were added 20.8 parts of hydroxylamine hydrochloride. Stirring was continued overnight at reflux temperature. The precipitated product was filtered off (the filtrate was set aside) and stirred in water. The filtrate, which was set aside (see above) was evaporated. The residue was stirred into water. The aqueous solutions were combined. The product was filtered off, washed with water and 2,2'-oxybispropane and dried in vacuo at 65° C., yielding 52.1 parts (89.3%) of (E+Z)-(3-methylphenyl) (3-pyridinyl)methanone,oxime; mp. 167.0° C. (intermediate 22).

In a similar manner there were also prepared: (E)-[2-(dimethoxymethyl)phenyl] (3-pyridinyl)methanone,oxime; mp. 124.2° C. (intermediate 23); and (E+Z)-[3-(dimethoxymethyl)phenyl] (3-pyridinyl)methanone,oxime; mp. 80.6° C. (intermediate 24).

EXAMPLE 10

A mixture of 9 parts of [3,5-bis(trifluoromethyl)phenyl] (3-pyridinyl)methanone, 2.09 parts of hydroxylamine hydrochloride, 2.46 parts of sodium acetate, 60 parts of methanol and 50 parts of water was stirred for 8 hours at reflux temperature. The ethanol layer was evaporated. The precipitated product was filtered off, washed successively with water, 2-propanol and 2,2'-oxybispropane and dried, yielding 7.6 parts (81%) of [3,5-bis(trifluoromethyl)phenyl] (3-pyridinyl)methanone,oxime; mp. 188° C. (intermediate 25).

In a similar manner there was also prepared: (E+Z)-(3-pyridinyl) [2-(trifluoromethyl)phenyl]methanone,oxime as a residue (intermediate 26).

EXAMPLE 11

A mixture of 40 parts of 2-phenyl-1-(3-pyridinyl)ethanone, 36.8 parts of 1-bromohexane, 25 parts of 2-methyl-2-propanol, potassium salt and 200 parts of dimethyl sulfoxide was stirred for 2 hours at room temperature under nitrogen atmosphere. The product was extracted with ethyl acetate. The extract was washed with a diluted sodium hydrogen carbonate solution, dried, filtered and evaporated. The residue was taken up in 160 parts of ethanol and 32 parts of hydroxylamine hydrochloride were added. After stirring for 1 hour at 50° C., the mixture was evaporated and the product was extracted with ethyl acetate. The extract was dried, filtered and evaporated. The residue was purified by column chromatography over silica gel using trichloromethane as eluent. The pure fractions were collected and the eluent was evaporated, yielding 7.8 parts (13%) of (E+Z)-2-phenyl-1-(3-pyridinyl)-1-octanone, oxime as a residue (intermediate 27).

B. Preparation of Final Compounds

EXAMPLE 12

To a stirred mixture of 5 parts of (E)-3-pyridinecarboxaldehyde, oxime and 90 parts of N,N-dimethylformamide were added portionwise 4.02 parts of a sodium hydride dispersion 50% at room temperature. Upon completion, stirring was continued at 40° C. till hydrogen gas evolution had ceased. After cooling, a solution of 8.3 parts of 6-bromohexanoic acid in 13.5 parts of N,N-dimethylformamide was added dropwise at 15° C. After complete addition, the reaction mixture was stirred for 30 minutes. It was poured into water and acidified with hydrochloric acid till pH=5. The precipitated product was filtered off and crystallized from a mixture of water and 2-propanol, yielding 6.37 parts (65.9%) of (E)-6-[[[(3-pyridinyl)methylen]amino]oxy]hexanoic acid; mp. 117.1° C. (compound 1).

In a similar manner there were also prepared: (E)-5-[[[(3-pyridinyl)methylen]amino]oxy]pentanoic acid; mp. 126.3° C. (compound 2); and (E)-3-[[[(3-pyridinyl)methylen]amino]oxy]propanoic acid; mp. 155.5° C. (compound 3).

EXAMPLE 13

To a stirred mixture of 8 parts of (E+Z)-phenyl(3-pyridinyl)methanone, oxime and 108 parts of N,N-dimethylformamide were added portionwise 4.0 parts of a sodium hydride dispersion 50% at room temperature. Upon completion, stirring was continued till hydrogen gas evolution had ceased. A solution of 8.3 parts of 5-bromopentanoic acid in 18 parts of N,N-dimethylformamide was added dropwise at room temperature. After complete addition, the reaction mixture was stirred and heated overnight at 80° C. The solvent was evaporated. The residue was taken up in a sodium hydrogen carbonate solution in water and extracted three times with dichloromethane. The pH of the separated aqueous/NaHCO$_3$ phase was brought to 5 with a hydrochloric acid solution. The product was extracted with dichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was taken up in 2-propanol and the latter was evaporated. The residue was stirred in a mixture of ethyl acetate and 2,2'-oxybispropane. The product was filtered off (the filtrate was set aside), washed with 2,2'-oxybispropane and dried in vacuo at 70° C., yielding a first fraction of 4.3 parts (35.8%) of (E+Z)-5-[[[phenyl(3-pyridinyl)methylen]amino]oxy]pentanoic acid; mp. 97.4° C. The filtrate, which was set aside, was evaporated. The residue was dried in vacuo at 60° C., yielding a second fraction of 0.8 parts (6.6%) of (E+Z)-5-[[[phenyl(3-pyridinyl)methylen]amino]oxy]pentanoic acid; mp. 92.4° C. (compound 4).

In a similar manner there were also prepared: (E+Z)-4-[[[phenyl(3-pyridinyl)methylen]amino]oxy]butanoic acid; mp. 88.2° C. (compound 5); and (E+Z)-6-[[[phenyl(3-pyridinyl)methylen]amino]oxy]hexanoic acid; mp. 104.1° C. (compound 6).

EXAMPLE 14

To a stirred mixture of 4.08 parts of (E)-1-(3-pyridinyl)ethanone, oxime and 45 parts of N,N-dimethylformamide were added portionwise 1.44 parts of a sodium hydride dispersion 50% at room temperature. The mixture was stirred till complete reaction and heated for a while in a water bath at 40°~50° C. After cooling, 6.9 parts of ethyl 5-bromopentanoate were added dropwise at room temperature (exothermic reaction). Upon completion, stirring was continued for 10 minutes. Upon standing overnight at room temperature, the reaction mixture was evaporated and water was added. The product was extracted with methylbenzene. The extract was dried, filtered and evaporated. The residue was purified by column chromatography over silica gel using a mixture of trichloromethane and methanol (95:5 by volume) as eluent. The pure fractions were collected and the eluent was evaporated, yielding 7.07 parts (89.5%) of ethyl (E)-5-[[[1-(3-pyridinyl)ethyliden]amino]oxy]pentanoate as a residue (compound 7).

In a similar manner there were also prepared:

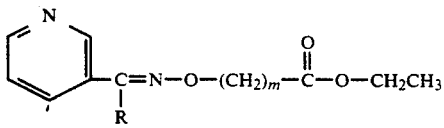

| No. | R | m | isomeric form | salt/base | mp (°C.) |
| --- | --- | --- | --- | --- | --- |
| 8 | H | 3 | E | .HCl | 105.6 |
| 9 | C6H5— | 4 | E | .base | — |
| 10 | C6H5— | 4 | Z | .base | — |
| 11 | C6H5—CH2— | 4 | E | .base | oil |
| 12 | 4-OCH3—C6H4— | 4 | E + Z | .base | — |
| 13 | 3-pyridinyl | 4 | — | .base | oil |
| 14 | 4-Cl—C6H4— | 4 | E + Z | .base | oil |
| 15 | 4-CH3—C6H4— | 4 | E + Z | .base | — |
| 16 | 4-F—C6H4— | 4 | E + Z | .base | — |
| 17 | 1-naphthalenyl | 4 | E + Z | .base | — |
| 18 | 2-thienyl | 3 | E | .base | — |
| 19 | 2-thienyl | 4 | E + Z | .base | — |
| 20 | CF3— | 4 | E + Z | .base | oil |
| 21 | 2-naphthalenyl | 4 | E + Z | .base | — |
| 22 | 4-NO2—C6H4— | 4 | E + Z | .base | — |
| 23 | 3,4-(OCH3)2—C6H3— | 4 | E + Z | .base | — |
| 24 | n-C4H9— | 4 | E + Z | .base | — |
| 25 | 2-[(OCH3)2CH]—C6H4— | 4 | E | .base | — |
| 26 | 3-CH3—C6H4— | 4 | E + Z | .base | — |
| 27 | 3-[(OCH3)2CH]—C6H4— | 4 | E + Z | .base | — |
| 28 | 2-CF3—C6H4— | 4 | E + Z | .base | — |
| 29 | 2-[(OCH3)2CH]—C6H4— | 4 | E + Z | .base | — |
| 30 | C6H5— | 4 | E + Z | .base | oil |

In a similar manner there are also prepared: ethyl 5-[[[(2-furanyl)(3-pyridinyl)methylen]amino]oxy]pentanoate (compound 31); ethyl 5-[[[(4-methoxy-1-naphthalenyl)(3-pyridinyl)methylen]amino]oxy]pentanoate (compound 32); ethyl 5-[[[(3-pyridinyl)(5-pyrimidinyl)-methylen]amino]oxy]pentanoate (compound 33); ethyl 5-[[[(3,4,5-trimethoxyphenyl)(3-pyridinyl)methylen]amino]oxy]pentanoate (compound 34); ethyl 5-[[[(2-(dimethoxymethyl)-1-naphthalenyl](3-pyridinyl)methylen]amino]oxy]pentanoate (compound 35); and ethyl 2-methyl-5-[[[(3-pyridinyl)[3-(trifluoromethyl)phenyl]-methylen]amino]oxy]pentanoate (compound 36).

EXAMPLE 15

To a stirred mixture of 10.2 parts of (E+Z)-(3-pyridinyl) (3-thienyl)methanone,oxime and 67.5 parts of N,N-dimethylformamide were added portionwise 2.4 parts of a sodium hydride dispersion 50% at room temperature during a period of 15 minutes. Upon completion, stirring was continued till hydrogen evolution had ceased. 12.5 Parts of ethyl 5-bromopentanoate were added dropwise during a period of 10 minutes. Upon complete addition, stirring was continued for 18 hours at room temperature. After evaporation in vacuo, the residue was stirred in water and the product was extracted with trichloromethane. The extract was dried, filtered and evaporated. The residue was purified twice by column chromatography over silica gel using a mixture of trichloromethane and ethyl acetate (90:10 by volume) as eluent. The first fraction was collected and the eluent was evaporated in vacuo, yielding 5.5 parts (33.0%) of ethyl (E)-5-[[[(3-pyridinyl) (3-thienyl)methylen]amino]oxy]pentanoate as a residue (compound 37). The second fraction was collected and the eluent was evaporated in vacuo, yielding 5 parts (30.0%) of ethyl (Z)-5-[[[(3-pyridinyl) (3-thienyl)methylen]amino]oxy]pentanoate as a residue (compound 38).

In a similar manner there were also prepared:

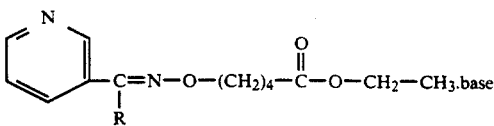

| No. | R | isomeric form |
| --- | --- | --- |
| 39 | 3-CF3—C6H4— | E |
| 40 | 2-thienyl | Z |
| 41 | 3-CH3—C6H4— | Z |
| 42 | 3-CH3—C6H4— | E |
| 43 | 3,5-(CF3)2—C6H3— | Z |
| 44 | 3,5-(CF3)2—C6H3— | E |
| 45 | 1-naphthalenyl | Z |
| 46 | 1-naphthalenyl | E |

EXAMPLE 16

A mixture of 7 parts of 2-phenyl-1-(3-pyridinyl)ethanone, oxime, 8.7 parts of ethyl 6-bromohexanoate, 10 parts of potassium carbonate and 45 parts of N,N-dimethylformamide was stirred overnight at room temperature. After evaporation, the residue was taken up in ethyl acetate. The organic phase was washed with as diluted sodium hydrogen carbonate solution in water, dried, filtered and evaporated. The residue was purified by column chromatography over silica gel using trichloromethane as eluent. The pure fractions were collected and the eluent was evaporated, yielding 12 parts (95%) of ethyl (E)-6-[[[2-phenyl-1-(3-pyridinyl)ethyliden]amino]oxy]hexanoate as a residue (compound 47).

In a similar manner there were also prepared:

| No. | R | m | isomeric form | mp (°C.) |
| --- | --- | --- | --- | --- |
| 48 | CH3 | 5 | — | — |
| 49 | CH3 | 3 | E | oil |
| 50 | n-C8H17— | 4 | E | — |
| 51 | n-C6H13— | 3 | E | — |
| 52 | n-C8H17— | 5 | E | oil |
| 53 | n-C6H13— | 4 | E | — |
| 54 | C6H5—CH2— | 3 | E | — |
| 55 | n-C6H13— | 5 | — | — |
| 56 | n-C3H7— | 3 | E | — |
| 57 | n-C8H17— | 3 | E | — |
| 58 | (3-pyridinyl)(CH3)2C— | 4 | — | — |
| 59 | (3-pyridinyl)(CH3)2C— | 3 | — | — |
| 60 | (3-pyridinyl)(CH3)2C— | 5 | — | — |
| 61 | (C6H5)(CH3)CH— | 5 | E + Z | — |

EXAMPLE 17

A mixture of 10 parts of (E+Z)-2-phenyl-1-(3-pyridinyl)-1-octanone, oxime, 7.5 parts of ethyl 6-bromohexanoate, 10 parts of potassium carbonate and 100 parts of dimethyl sulfoxide was stirred overnight at room temperature. The product was extracted with 1,1'-oxybisethane. The extract was washed with water, dried, filtered and evaporated. The residue was purified by column chromatography over silica gel using trichloromethane as eluent. The pure fractions were collected and the eluent was evaporated, yielding 10 parts (68%) of ethyl (E+Z)-6-[[[2-phenyl-1-(3-pyridinyl)oc-tyliden]amino]oxy]hexanoate as a residue (compound 62).

EXAMPLE 18

A mixture of 4.3 parts of ethyl (E)-5-[[[(3-pyridinyl)[3-(trifluoromethyl)phenyl]methylen]amino]oxy]pentanoate, 25 parts of a sodium hydroxide solution 1N and 20 parts of ethanol was stirred for 2.5 hours at room temperature. 25 Parts of a hydrochloric acid solution 1N were added and the ethanol layer was evaporated. The product was extracted with dichloromethane. The extract was dried, filtered and evaporated. The residue was purified by column chromatography over silica gel using a mixture of trichloromethane and methanol (98:2 by volume) as eluent. The pure fractions were collected and the eluent was evaporated. The residue was crystallized from a mixture of 2,2'-oxybispropane and hexane (2:1 by volume). The product was filtered off and dried, yielding 1.7 parts (42.2%) of (E)-5-[[[(3-pyridinyl)[3-(trifluoromethyl)phenyl]methylen]amino]oxy]pentanoic acid; mp. 70.3° C. (compound 63).

In a similar manner there were also prepared:

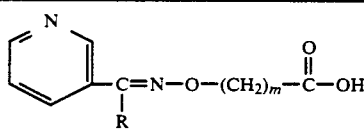

| No. | R | m | isomeric form | salt/base | mp (°C.) |
|---|---|---|---|---|---|
| 64 | H— | 3 | E | .base | 128.2 |
| 65 | C$_6$H$_5$— | 4 | E | .base | 114.3 |
| 66 | C$_6$H$_5$— | 4 | E | .base | 107.0 |
| 67 | CH$_3$— | 4 | E | .base | 103.5 |
| 68 | C$_6$H$_5$—CH$_2$— | 4 | E | .base | 78.4 |
| 69 | 4-OCH$_3$—C$_6$H$_4$— | 4 | E + Z | .base | 99.7 |
| 70 | 3-pyridinyl | 4 | — | .base | 84.7 |
| 71 | 4-Cl—C$_6$H$_4$— | 4 | E + Z | .base | 81.7 |
| 72 | 4-CH$_3$—C$_6$H$_4$— | 4 | E + Z | .base | 83.4 |
| 73 | 4-F—C$_6$H$_4$— | 4 | E + Z | .base | 73.1 |
| 74 | 1-naphthalenyl | 4 | E + Z | .base | 115.1 |
| 75 | 2-thienyl | 4 | E | .base | 121.9 |
| 76 | 2-thienyl | 4 | Z | .base | 95.1 |
| 77 | CF$_3$— | 4 | E + Z | .base | 58.2 |
| 78 | 2-naphthalenyl | 4 | E + Z | .base | 108.5 |
| 79 | 4-NH$_2$—C$_6$H$_4$— | 4 | E + Z | .base | 139.4 |
| 80 | C$_6$H$_5$—CH$_2$— | 3 | E | .base | 89.6 |
| 81 | 4-NO$_2$—C$_6$H$_4$— | 4 | E + Z | .base | 93.9 |
| 82 | 3,4-(OCH$_3$)$_2$—C$_6$H$_3$— | 4 | E + Z | .base | 102.5 |
| 83 | 3-thienyl | 4 | E | .base | 98.6 |
| 84 | 3-thienyl | 4 | Z | .base | 90.5 |
| 85 | 3-CF$_3$—C$_6$H$_4$— | 4 | Z | .base | 84.7 |
| 86 | n-C$_4$H$_9$— | 4 | E | .(COOH)$_2$ | 89.2 |
| 87 | 2-[(OCH$_3$)$_2$CH]—C$_6$H$_4$— | 4 | E | .(COOH)$_2$ | 132.2 |
| 88 | 3-CH$_3$—C$_6$H$_4$— | 4 | Z | .base | 80.8 |
| 89 | 3-CH$_3$—C$_6$H$_4$— | 4 | E + Z | .base | 62.0 |
| 90 | 3-CH$_3$—C$_6$H$_4$— | 4 | E | .base | 99.6 |
| 91 | 3,5-(CF$_3$)$_2$—C$_6$H$_3$— | 4 | Z | .base | 110.0 |
| 92 | 3,5-(CF$_3$)$_2$—C$_6$H$_3$— | 4 | E | .base | 115.5 |
| 93 | 1-naphthalenyl | 4 | E | .base | 128.8 |
| 94 | 2-CF$_3$—C$_6$H$_4$— | 4 | E + Z | .base | 83.3 |
| 95 | 1-naphthalenyl | 4 | Z | .base | 118.6 |

In a similar manner there are also prepared: 5-[[[(2-furanyl)(3-pyridinyl)methylen]amino]oxy]pentanoic acid (compound 96); 5-[[[(4-methoxy-1-naphthalenyl)(3-pyridinyl)methylen]amino]oxy]pentanoic acid (compound 97); 2-methyl-5-[[[(3-pyridinyl)[3-(trifluoromethyl)phenyl]methylen]amino]oxy]pentanoic acid (compound 98); 5-[[[(3-pyridinyl)(5-pyrimidinyl)methylen]amino]oxy]pentanoic acid (compound 99); and 5-[[[(3,4,5-trimethoxyphenyl)(3-pyridinyl)methylen]amino]oxy]pentanoic acid (compound 100).

EXAMPLE 19

A mixture of 6 parts of ethyl 5-[[[2-methyl-1,2-di(3-pyridinyl)propyliden]amino]oxy]pentanoate and 80 parts of a sodium hydroxide solution 3N was stirred for 12 hours at room temperature. The reaction mixture was acidified with a hydrochloric acid solution 3N. After evaporation to dry, the residue was taken up in methanol and the precipitate was filtered off. The filtrate was evaporated and the residue was purified by column chromatography over silica gel using a mixture of trichloromethane, methanol and formic acid (90:10:1 by volume) as eluent. The pure fractions were collected and the eluent was evaporated. The residue was converted into the ethanedioate salt in a mixture of 2-propanone and methanol. The salt was filtered off and dried, yielding 4.2 parts (50%) of 5-[[[2-methyl-1,2-di(3-pyridinyl)propyliden]amino]oxy]pentanoic acid ethanedioate(1:2); mp. 134.8° C. (compound 101).

In a similar manner there were also prepared:

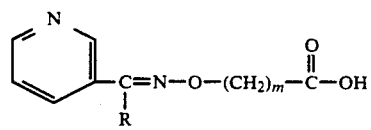

| No. | R | m | isomeric form | salt/base | mp (°C.) |
|---|---|---|---|---|---|
| 102 | CH$_3$— | 5 | — | .base | 95.1 |
| 103 | CH$_3$— | 3 | E | .base | 105.3 |
| 104 | n-C$_8$H$_{17}$— | 4 | E | .(COOH)$_2$ | 109.3 |
| 105 | n-C$_6$H$_{13}$— | 3 | E | .(COOH)$_2$ | 113.1 |
| 106 | n-C$_8$H$_{17}$— | 5 | E | .(COOH)$_2$ | 114.0 |
| 107 | n-C$_6$H$_{13}$— | 4 | E | .(COOH)$_2$ | 93.0 |
| 108 | n-C$_6$H$_{13}$— | 5 | E + Z | .(COOH)$_2$ | 108.1 |
| 109 | n-C$_3$H$_7$— | 3 | E | .1½(COOH)$_2$ | 117.4 |
| 110 | C$_6$H$_5$—CH$_2$— | 5 | E | .base | 73.0 |
| 111 | n-C$_8$H$_{17}$— | 3 | E | .(COOH)$_2$ | 106.7 |
| 112 | (3-pyridinyl)(CH$_3$)$_2$C— | 3 | — | .2(COOH)$_2$ | 121.9 |
| 113 | (3-pyridinyl)(CH$_3$)$_2$C— | 5 | — | .1½(COOH)$_2$ | 139.6 |
| 114 | 1-(C$_6$H$_5$)-n-heptyl | 5 | E + Z | .base | 90.4 |

EXAMPLE 20

A mixture of 7.4 parts of (E+Z)-5-[[[(3-pyridinyl)[3-(trifluoromethyl)phenyl]methylen]amino]oxy]pentanoic acid, 2.16 parts of sulfuric acid, 80 parts of methanol and 21.3 parts of 2,2-dimethoxypropane was stirred for 1 hour at reflux temperature. After concentration, crushed ice was added to the concentrate, followed by the addition of ammonium hydroxide. The product was extracted with dichloromethane. The extract was dried, filtered and concentrated. The residue was purified twice by column chromatography over silica gel using a mixture of trichloromethane and acetonitrile (80:20 and 85:15 by volume) as eluents. The pure fractions were collected and the eluent was evaporated, yielding 4.7 parts (61%) of methyl (E)-5-[[[(3-pyridinyl)[3-(trifluoromethyl)phenyl]methylen]amino]oxy]pentanoate as a residue (compound 115).

EXAMPLE 21

A mixture of 2.6 parts of ethyl (E+Z)-5-[[[[3-(dimethoxymethyl)phenyl](3-pyridinyl)methylen]amino]oxy]pentanoate, 15 parts of a hydrochloric acid solution 1N and 13.5 parts of tetrahydrofuran was stirred for 2 days at room temperature (exothermic reaction: the temperature rose to 40° C.). Another portion of 15 parts of a hydrochloric acid solution 1N and 13.5 parts of tetrahydrofuran were added. After complete reaction, 30 parts of a sodium hydroxide solution 1N were added and then the tetrahydrofuran layer was evaporated. The aqueous phase was extracted with dichloromethane. The organic layer was dried, filtered and evaporated. The residue was purified by column chromatography over silica gel using a mixture of trichloromethane and methanol (90:10 by volume) as eluent. The pure fractions were collected and the eluent was evaporated. The residue was allowed to crystallize at room temperature. The product was taken up in a mixture of ethyl acetate and 2,2'-oxybispropane. The product was filtered off, washed with 2,2'-oxybispropane and dried in vacuo at 60° C., yielding 0.55 parts (26.3%) of (E+Z)-5-[[[(3-formylphenyl)(3-pyridinyl)methylen]amino]oxy]pentanoic acid; mp. 111.4° C. (compound 116).

In a similar manner there is also prepared: 5-[[[(2-formyl-1-naphthalenyl)(3-pyridinyl)methylen]amino]oxy]pentanoic acid (compound 117).

EXAMPLE 22

A mixture of 5.7 parts of ethyl (E+Z)-5-[[[(4-nitrophenyl) (3-pyridinyl)methylen]amino]oxy]pentanoate, 13 parts of sodium dithionite, 80 parts of ethanol and 65 parts of water was stirred for 7 hours at room temperature (slightly exothermic reaction). The mixture was allowed to stand overnight. After evaporation, water was added and the product was extracted with dichloromethane. The extract was dried, filtered and concentrated. The concentrate was purified by column chromatography over silica gel using a mixture of trichloromethane and methanol (95:5 by volume) as eluent. The pure fractions were collected and the eluent was evaporated, yielding 1.7 parts (33.1%) of ethyl (E+Z)-5-[[[(4-aminophenyl)(3-pyridinyl)methylen]amino]oxy]pentanoate as a residue (compound 118).

EXAMPLE 23

To a stirred solution of 1.7 parts of (E+Z)-5-[[[(4-aminophenyl) (3-pyridinyl)methylen]amino]oxy]pentanoic acid in 22.5 parts of tetrahydrofuran were added dropwise 0.56 parts of acetic acid anhydride at room temperature. Upon complete addition, stirring was continued for 2.5 hours at room temperature. The mixture was allowed to stand over weekend at room temperature. After evaporation, the residue was purified by column chromatography over silica gel using a mixture of trichloromethane and methanol (90:10 by volume) as eluent. The pure fractions were collected and the eluent was evaporated. The residue was stirred in 100 parts of a mixture of methylbenzene and 2,2'-oxybispropane (25:75 by volume). The product was filtered off, washed with 2,2'-oxybispropane and dried, yielding 1.2 parts (67.5%) of (E+Z)-5-[[[[4-acetylamino)phenyl](3-pyridinyl)methylen]amino]oxy]pentanoic acid; mp. 112.9° C. (compound 119).

EXAMPLE 24

A mixture of 7.6 parts of ethyl (E+Z)-6-[[[2-phenyl-1-(3-pyridinyl)propyliden]amino]oxy]hexanoate and 100 parts of a sodium hydroxide solution 3N was stirred overnight at room temperature. The reaction mixture was neutralized with a hydrochloric acid solution 3N to pH 5.5. The reaction mixture was concentrated and the concentrate was dissolved in 2-propanone. The inorganic salts were filtered off and the filtrate was dried, filtered and evaporated. The residue was purified by column chromatography over silica gel using a mixture of trichloromethane and ethyl acetate (95:5 by volume) as eluent. The pure fractions were collected and the eluent was evaporated. The residue was dissolved in a solution of 0.56 parts of sodium in methanol. After evaporation to dry, the residue was suspended in 1,1'-oxybisethane during 1 hour. The product was filtered off and dried in vacuo, yielding 2.8 parts (38%) of sodium (E+Z)-6-[[[2-phenyl-1-(3-pyridinyl)propyliden]amino]oxy]hexanoate; mp. 190.7° C. (compound 120).

EXAMPLE 25

To a stirred solution of 1 part of (E)-5-[[[(3-pyridinyl)[3-(trifluoromethyl)phenyl]methylen]amino]oxy]pentanoic acid in 40 parts of methanol were added 2.94 parts of a sodium methoxide solution in methanol. The reaction mixture was evaporated. The precipitated product was filtered off and dried at 60° C., yielding 0.6 parts (56.5%) of sodium (E)-5-[[[(3-pyridinyl)[3-(trifluoromethyl)phenyl]methylen]amino]oxy]pentanoate; mp. 215.9° C. (compound 121).

In a similar manner there were also prepared: sodium (E)-5-[[[phenyl(3-pyridinyl)methylen]amino]oxy]pentanoate; mp. 153.4° C. (compound 122); sodium (E)-5-[[[(1-naphthalenyl)(3-pyridinyl)methylen]amino]oxy]pentanoate; mp. 172.0° C. (compound 123); and In a similar manner there is also prepared: sodium 5-[[[(4-methoxy-1-naphthalenyl)(3-pyridinyl)methylen]amino]oxy]pentanoate (compound 124).

EXAMPLE 26

To a stirred solution of 1 part of (E)-5-[[[(1-naphthalenyl) (3-pyridinyl)methylen]amino]oxy]pentanoic acid in 75 parts of trichloromethane were added portionwise 0.625 parts of 3-chlorobenzenecarboperoxoic acid at 0°~5° C. Upon complete addition, the reaction mixture was allowed to reach room temperature overnight. After evaporation, the residue was crystallized twice from ethyl acetate. The product was filtered off, washed with ethyl acetate and 2,2'-oxybispropane and dried in vacuo at 50° C., yielding 0.64 parts (61.1%) of (E)-5-[[[(1-naphthalenyl)(3-pyridinyl)methylen]amino]oxy]pentanoic acid,N-oxide; mp. 165.6° C. (compound 125).

EXAMPLE 27

A mixture of 6.5 parts of silver(I) oxide, 50 parts of water, 63 parts of ethanol and 6.5 parts of 5-[[[(3-formylphenyl)(3-pyridinyl)methylen]amino]oxy]pentanoic acid is stirred for 1 hour at a somewhat elevated temperature to give 3-[[(4-carboxybutoxy)imino](3-pyridinyl)methyl]benzoic acid (compound 126).

C. Pharmacological Examples

EXAMPLE 28

Platelet Malondialdehyde (MDA) Production

MDA production by platelets in plasma, as an indicator of the thromboxane $A_2$ biosynthesis, was evaluated spectrofluometrically. 0.4 ml of citrated platelet-rich plasma ($250 \times 10^3$ platelets/$\mu$l) in the presence of solvent (dimethylsulfoxide 0.2%) or compound solution was pre-incubated for 10 min at 37° C. and then challenged with 50 $\mu$l of $CaCl_2$ 1 mM final concentration and 50 μl of trombin 20 N.I.H. U/ml final concentration. After 30 min at 37° C., the reaction was terminated by the addition of 1 ml of 10% (w/v) trichloroacetic acid. After isolation of the supernatant by centrifugation at 320 g for 20 min, the thiobarbituric acid reaction for MDA was performed using acid-hydrolyzed 1,1,3,3-tetramethoxypropane as a standard. The fluorescence of the samples at 553 nm after excitation at 510 nm was measured. The results were calculated as nM MDA/$10^8$ platelets/30 min and were expressed as a percentage inhibition produced by the compounds relative to the formation of MDA after thrombin stimulation in the solvent. For in vitro experiments, human platelets in plasma were used. Percentage inhibition was calculated versus the solvent value. $IC_{50}$-values were determined as those doses in μM causing of 50% inhibition.

For in vivo experiments male Wistar rats were fasted overnight. 2 Hours before blood sampling they were treated with the test compound solution/suspension of the solvent. A 50% inhibition relative to the MDA values obtained with the solvent was considered as the criterion of inhibitory activity. $ED_{50}$-values were determined by probit analysis. Said $IC_{50}$-values and $ED_{50}$-values of a number of compounds of formula (I) are depicted in the table below. The compounds in this table are not given for the purpose of limiting the invention thereto but only to exemplify the useful pharmacological properties of all the compounds within the scope of formula (I).

| Compound No. | MDA production in vitro $IC_{50}$-values in μM | MDA production in vivo $ED_{50}$-values in mg/kg body weight |
| --- | --- | --- |
| 4 | 0.10 | 0.059 |
| 9 | <0.1 | — |
| 65 | 0.066 | 0.045 |
| 68 | 0.075 | 1.0 |
| 69 | 0.1 | 0.17 |
| 70 | 0.18 | 1.2 |
| 72 | 0.12 | 0.041 |
| 63 | 0.022 | 0.012 |
| 73 | 0.30 | 0.20 |
| 74 | 0.023 | 0.023 |
| 76 | 0.12 | 0.068 |
| 78 | 0.24 | 0.044 |
| 82 | 0.11 | 0.056 |
| 84 | 0.11 | 0.17 |
| 86 | 0.063 | >0.16 |
| 87 | 0.024 | >0.16 |
| 122 | 0.081 | <0.16 |
| 89 | 0.043 | 0.02 |
| 90 | 0.024 | 0.013 |
| 92 | 0.033 | 0.01 |
| 116 | 0.1 | — |
| 93 | 0.010 | 0.014 |
| 94 | 0.032 | — |
| 123 | 0.018 | — |
| 121 | 0.014 | 0.015 |

D. Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or pharmaceutically acceptable acid addition salt thereof.

EXAMPLE 29

Oral Drops

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

EXAMPLE 30

Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

EXAMPLE 31

Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

EXAMPLE 32

Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®)) in about 200 milliliters of water. The wet powder mixture was sieved, dried and sieved again. Then there was added 100 grams microcrystalline cellulose (Avicel ®)) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetrio. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated.

The tablet cores were coated with the thus obtained mixture in a coating apparatus.

EXAMPLE 33

Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

EXAMPLE 34

Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°-38° C. to form 100 suppositories each containing 30 milligrams of the active ingredient.

What we claim is:

1. A compound of the formula:

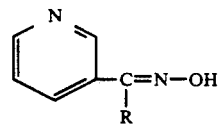

an N-oxide form, an alkali or alkaline earth metal substitution salt, or a stereochemically isomeric form thereof, wherein:

R represents phenyl or naphthalenyl wherein said phenyl and naphthalenyl are each optionally substituted with up to 2 substituents being each independently selected from the group consisting of $C_{1-6}$alkyloxy, di($C_{1-6}$alkyloxy)methyl, formyl, and trifluoromethyl provided that R represents other than unsubstituted phenyl.

2. A compound according to claim 1 wherein the compound is in the (E+Z)-form.

3. A compound according to claim 1 wherein the compound is in the (E)-form.

4. A compound according to claim 1 wherein the compound is in the (Z)-form.

5. A compound according to claim 1 wherein the compound is in the form of a metal substitution salt.

6. A compound according to claim 1 wherein the compound is (E+Z)-(3-pyridinyl)[3-(trifluoromethyl)phenyl]methanone, oxime; (E+Z)-[3,5-bis(trifluoromethyl)phenyl](3-pyridinyl)methanone, oxime or (E+Z)-(3-pyridinyl)[2-(trifluoromethyl)phenyl]methanone, oxime.

7. A compound according to claim 1 wherein the compound is (E+Z)-(4-methoxyphenyl)(3-pyridinyl)methanone, oxime; or (E+Z)-(3,4-dimethoxyphenyl)(3-pyridinyl)methanone, oxime.

8. A compound according to claim 1 wherein the compound is (E+Z)-[3-(dimethoxymethyl)phenyl](3-pyridinyl)methanone, oxime; or (E)-[2-dimethoxymethyl)phenyl](3-pyridinyl)methanone, oxime.

9. A compound according to claim 1 wherein the compound is (E+Z)-(1-naphthalenyl)(3-pyridinyl)methanone, oxime; or (E+Z)-(2-naphthalenyl)(3-pyridinyl)methanone, oxime.

* * * * *